(12) United States Patent
Svanbäck

(10) Patent No.: US 10,520,411 B2
(45) Date of Patent: Dec. 31, 2019

(54) METHOD AND SYSTEM FOR DETERMINING DISSOLUTION PROPERTIES OF MATTER

(71) Applicant: Sami Svanbäck, Helsinki (FI)

(72) Inventor: Sami Svanbäck, Helsinki (FI)

(73) Assignee: The Solubility Company Oy, Helsinki (FI)

( * ) Notice: Subject to any disclaimer, the term of this patent is extended or adjusted under 35 U.S.C. 154(b) by 87 days.

(21) Appl. No.: 15/506,766

(22) PCT Filed: Aug. 31, 2015

(86) PCT No.: PCT/FI2015/050562
§ 371 (c)(1),
(2) Date: Feb. 27, 2017

(87) PCT Pub. No.: WO2016/030583
PCT Pub. Date: Mar. 3, 2016

(65) Prior Publication Data
US 2018/0231446 A1    Aug. 16, 2018

(30) Foreign Application Priority Data
Aug. 29, 2014  (FI) ..................................... 20145751

(51) Int. Cl.
*G01N 13/02* (2006.01)
*B01F 1/00* (2006.01)
(Continued)

(52) U.S. Cl.
CPC ........... *G01N 13/02* (2013.01); *B01F 1/0027* (2013.01); *B01F 5/006* (2013.01); *B01F 5/0057* (2013.01);
(Continued)

(58) Field of Classification Search
CPC .... G01N 13/02; G01N 13/00; G01N 15/0227; G01N 33/15; G01N 2013/006;
(Continued)

(56) References Cited

U.S. PATENT DOCUMENTS 6,497,157 B1    12/2002  Viegas et al.
7,021,163 B2 *   4/2006  Kyne ..................... G01N 33/15
                                                   73/866

(Continued)

FOREIGN PATENT DOCUMENTS

EP         2749866 A1     7/2014
WO    WO 9746860 A2    12/1997
(Continued)

OTHER PUBLICATIONS

Arifin, D. et al.: "Microfluidic blood plasma separation via bulk electrohydrodynamic flows", Biomicrofluidics 1, 014103, 2007, pp. 1-13.

(Continued)

*Primary Examiner* — Daniel S Larkin
(74) *Attorney, Agent, or Firm* — Seppo Laine Oy

(57) ABSTRACT

The invention concerns a method and system for determining dissolution properties of a particle. The method comprises providing into a vessel dissolution medium capable of dissolving the particle and providing the particle into said vessel in contact with the dissolution medium for dissolving the particle. According to the invention, the particle is trapped in a particle trapping zone formed at a predetermined location in the vessel, the particle trapping zone being formed preferably at least partially by continuous hydrodynamic motion of the dissolution medium. Residue of the particle is imaged while being trapped in said particle trapping zone for providing a plurality of sequential images of the particle residue. Finally, at least one dissolution (Continued)

property of the particle is determined based on the sequential images. The invention allows for dissolution rate, intrinsic dissolution rate and/or solubility of matter to be reliably determined from very small sample amounts and without manual affixation of samples.

22 Claims, 6 Drawing Sheets

(51) Int. Cl.

| | | |
|---|---|---|
| *B01F 5/00* | (2006.01) | |
| *B01L 3/00* | (2006.01) | |
| *G01N 15/02* | (2006.01) | |
| *G01N 33/15* | (2006.01) | |
| *G01N 13/00* | (2006.01) | |

(52) U.S. Cl.
CPC .............. *B01L 3/502* (2013.01); *G01N 13/00* (2013.01); *G01N 15/0227* (2013.01); *G01N 33/15* (2013.01); *B01L 2300/0861* (2013.01); *B01L 2300/0864* (2013.01); *B01L 2400/086* (2013.01); *G01N 2013/006* (2013.01)

(58) Field of Classification Search
CPC .. B01F 1/0027; B01F 5/0057; B01F 5/00577; B01F 5/006; B01L 3/502
USPC ........................................................ 73/61.71
See application file for complete search history.

(56) References Cited

U.S. PATENT DOCUMENTS

| | | | |
|---|---|---|---|
| 9,418,416 B2* | 8/2016 | Milne ................ | G01N 21/9027 |
| 2001/0051124 A1* | 12/2001 | Woerlee ................ | B01F 1/0022 |
| | | | 423/293 |
| 2009/0207691 A1 | 8/2009 | Fetvedt | |
| 2010/0209927 A1 | 8/2010 | Menon et al. | |
| 2010/0262381 A1 | 10/2010 | Zeng | |
| 2010/0288043 A1 | 11/2010 | Manalis et al. | |
| 2010/0288944 A1 | 11/2010 | Avdeef et al. | |
| 2012/0134230 A1 | 5/2012 | Engelhardt et al. | |
| 2013/0171628 A1 | 7/2013 | Di Carlo et al. | |
| 2014/0033808 A1 | 2/2014 | Ding et al. | |

FOREIGN PATENT DOCUMENTS

| | | |
|---|---|---|
| WO | WO 03102737 A2 | 12/2003 |
| WO | WO 2008068680 A2 | 6/2008 |
| WO | WO 2010006166 A2 | 1/2010 |
| WO | WO 2013130714 A1 | 9/2013 |
| WO | WO 2013177560 A1 | 11/2013 |

OTHER PUBLICATIONS

Avdeef, A. et al.: "Miniaturization of Powder Dissolution Measurement and Estimation of Particle Size", Chemistry & Biodiversity, vol. 6, 2009, pp. 1796-1811.

Börjesson, E. et al.: "The dissolution behavior of individual powder particles", Dairy Science & Technology, 2013, pp. 357-371.

Crist, G. B.: "2009 Trends in small-volume dissolution apparatus for low-dose sompounds, dissolution technologies", Dissolution Technologies, Feb. 2009, pp. 19-22.

Hulse, W. et al.: "A discriminatory intrinsic dissolution study using UV area imaging analysis to gain additional insights into the dissolution behaviour of active pharmaceutical ingredients", International Journal of Pharmaceutics 434, 2012, pp. 133-139.

Marabi, A. et al.: "Assessing dissolution kinetics of powders by a single particle approach", Chemical Engineering Journal 139, 2008, pp. 118-127.

Mosharraf, M. et al.: "The effect of particle size and shape on surface specific dissolution rate of microsized practically insoluble drugs", International Journal of Pharmaceutics 122, 1995, pp. 35-47.

Prasad, K.V.R.et al.: "Dissolution kinetics of paracetamol single crystals", International Journal of Pharmaceutics 238, 2002, pp. 29-41.

Scheubel, E. et al.: "Small Volume Dissolution Testing as a Powerful Method during Pharmaceutical Development", Pharmaceutics 2010, vol. 2, pp. 351-363.

Svanbäck, S. et al.: "Optical microscopy as a comparative analytical technique for single-particle dissolution studies", International Journal of Pharmaceutics 469, 2014, pp. 10-16.

Tsinman, K. et al.: "Powder Dissolution Method for Estimating Rotating Disk Intrinsic Dissolution Rates of Low Solubility Drugs", Pharmaceutical Research, vol. 26, No. 9, Sep. 2009, pp. 2093-2100.

* cited by examiner

METHOD AND SYSTEM FOR DETERMINING DISSOLUTION PROPERTIES OF MATTER

FIELD OF THE INVENTION

The invention relates to analyzing dissolution properties of matter. In particular, the invention relates to a method for determining the dissolution rate, intrinsic dissolution rate and/or solubility of particles. The invention also relates to a corresponding system and components thereof.

BACKGROUND OF THE INVENTION

Pharmaceutical substances need to be in dissolved state in order to be able to have an influence in human or animal body. Because of this, dissolution properties of solid-state pharmaceutical substances is one of the most important targets of studying in pharmaceutical research and development. In early development phase of new drugs, the number of candidate compounds is very large but the amount of each compound available is very small. Thus, traditional dissolution rate and solubility tests cannot be made. This problem field is discussed e.g. in Lipinski C A, et al: *Experimental and computational approaches to estimate solubility and permeability in drug discovery and development settings.* Adv Drug Deliv Rev 46: 3-26, 2000.

Other relatively current dissolution testing instruments and challenges of small-volume dissolution testing in pharmaceutical development are presented in Crist G. B., 2009 *Trends in Small-Volume Dissolution Apparatus for Low-Dose Compounds, Dissolution Technologies*, February 2009 and Scheubel E. et al, *Small Volume Dissolution Testing as a Powerful Method during Pharmaceutical Development, Pharmaceutics* 2010, 2, 351-363; doi:10.3390/pharmaceutics2040351.

In modern drug development, qualitative methods which guide the development process, are used. Such methods include kinetic solubility tests and computer simulations. These methods can be used to roughly rank different agents based on solubility estimates obtained. However, the qualitative methods suffer from severe drawbacks and it is not uncommon to obtain for example a solubility estimate which deviates from the real solubility by a factor of ten.

There are no methods available which suit for dissolution property testing of large numbers of very small sample amounts, such as individual particles of the substance of interest. Using chemical analysis, it is demanding and resource consuming to get accurate results using small sample amounts. In addition, the chemical analysis methods are specific to the substance used, and therefore non-universal, raising the need for substance consuming and specific method development with continuous validation of new testing methods.

There are also microscopic methods, which utilize manual affixation of the particles by clamping or gluing to a support, and imaging the particles as they dissolve in the affixed position. While microscopic imaging is a non-specific method compared with chemical analysis and suits for all substances, these methods are, however laborious and therefore unsuited for drug development involving a high number of samples. The main problem in these methods is the affixation of the samples so that they both dissolve, i.e. come in contact with the solvent used, and are simultaneously able to be imaged. This would need to be done in very short time frame and with as little human interaction as possible, which has proven to be challenging. In addition, the surface or structure of the particles may be damaged during the affixation process.

An article by Svanbäck, S., et al., Optical microscopy as a comparative analytical technique for single-particle dissolution studies, Int J Pharmaceut (2014), http://dx.doi.org/10.1016/j.ijpharm.2014.04.036, widely discusses the option to use optical microscopy for particle dissolution studies. In particular, it is demonstrated that data obtained by optical digital microscopy and UV-spectrophotometry, as a widely-used representative of chemical analysis methods, produce practically identical dissolution curves, with equal variance, for dissolving single particles of model acidic and basic drug compounds. Thus, image analysis can indeed be used, on its own, as a viable analytical technique in single-particle dissolution studies. However, Svanbäck et al. describes a method for characterizing the dissolution rate from an individual particle in a stagnant liquid. The particle in such stagnant system is not trapped, rather immovable or fixed. An essential feature of dissolution property characterization is the capability of changing the flow rate of the dissolution medium, during or between experiments, and the capability of characterizing a particle/s in a stagnant or flowing medium. Thus, the problem relating to maintaining the particle in a fixed position for fast imaging remains.

US 2010/288043 relates to method and apparatus for improving measurements of particle or cell characteristics, such as mass, in Suspended Microchannel Resonators (SMR's), and describes several methods for mechanical trapping of particles or cells. Imaging in the device of this US-application is used as a feedback for the trapping, not for characterization of the particles. In the device changing of flow directions is necessary for the hydrodynamic trapping of particles. This is, however, disadvantageous in dissolution property characterization, as the flow rate and direction directly influences the acquired data.

Thus, there is a need for improved imaging-based dissolution testing methods.

SUMMARY OF THE INVENTION

It is an aim of the invention to provide a novel method for determining dissolution properties of particulate substances, such as dissolution rate of pharmaceutical agents, of small sample amounts. A particular aim is to provide a method suitable for individual particles.

It is also an aim of the invention to provide a system for determining dissolution properties of dissolvable particulate matter.

A particular aim is to provide a method and system capable of determining dissolution rate, intrinsic dissolution rate and/or solubility of the particles.

The invention is based on the idea of carrying out a dissolution test for one or more particles, which is/are trapped to a desired location in a dissolution vessel without mechanically clamping it/them to the vessel, by imaging. In particular, the trapping may at least partly, preferably entirely, be achieved by hydrodynamic fluid motion in the vessel. Thus, the dissolution fluid flows inside the vessel such that if forms a trapping zone, where particles guided to the vessel seek their way and remain positioned while sequential images are taken thereof through the vessel wall. The sequential images are then analyzed using a computer to derive the desired dissolution property, such as dissolution rate, intrinsic dissolution rate (IDR) or solubility.

To give a more concrete example, in one implementation of the invention, the invention takes advantage of the same phenomena as in the so-called "Einstein's teacup", i.e., tea leafs (particles) tend to move to the centre and bottom zone (trapping zone) of the teacup (vessel) while stirred. In particular, it has been found by the inventors that several vessel design and solvent flow combinations can be found where the trapping zone is stable enough for particles rotating therein to be imaged several times and from different angles. The particle can be e.g. a chemical, biological or biochemical particle and in particular a pharmaceutical substance or a candidate for a pharmaceutical substance.

Thus, the method according to the invention for determining dissolution properties of a particle comprises of providing into a vessel dissolution medium capable of dissolving the particle and providing the particle into said vessel in contact with the dissolution medium for dissolving the particle. According to the invention, the particle is trapped in a particle trapping zone formed at a predetermined location in the vessel, the particle trapping zone being formed preferably at least partially by continuous hydrodynamic motion of the dissolution medium. Residue of the particle is imaged while being trapped in said particle trapping zone for providing a plurality of sequential images of the particle residue. Finally, at least one dissolution property of the particle is determined based on the sequential images.

The present system for determining dissolution properties of a particle comprises a dissolution vessel comprising a dissolution chamber capable of holding dissolution medium, and means for providing a flow of dissolution medium in the dissolution chamber. The dissolution medium can be one or many liquids, either pre-mixed or continuously mixed in desired ratios during a test. Gradient runs and changing of medium is thus possible during experiments. According to the invention the system is provided with means for producing a particle trapping zone in the dissolution chamber, where the particle remains essentially in a steady position. Imaging can be performed from one or more directions using an imaging system integrated into the vessel walls. In addition, the dissolution vessel may comprise at least one transparent portion allowing for imaging of a particle trapped in the particle trapping zone from outside of the vessel. The chamber and means for producing a particle trapping zone in the dissolution chamber are preferably at least partially based on producing such a hydrodynamic flow inside the chamber that keeps the particle essentially at a steady position inside the chamber.

More specifically, the invention is characterized by what is stated in the independent claims.

The invention provides considerable advantages. Unlike existing dissolution property testing methods, it does not require substance-specific validation or use of specific chemical analytical methods. The invention is also suited for smaller sample amounts. Additionally, unlike existing microscopic methods, the invention does not necessitate manual or mechanical affixation of the particles to be tested. Thus, problems relating to damaging of the samples and vast amounts of manual work are avoided. The sample is simply conducted to a suitable vessel, where it is trapped using a liquid flow to a stabile position allowing for imaging. No mechanical affixation such as gluing or clamping is needed.

The invention is suitable for individual fine particles of the matter of interest. Still, reliable information on the dissolution behavior of the matter is obtained, which is of great advantage in pharmaceutical development.

An advantage of the invention is also that the sample particles can be imaged from many directions during the dissolution process, since there are no mechanical members that engage the particle. For example, a particle trapped in a rotating flow can be imaged from many views using a camera on one side of the vessel only, as the particle (or its residue) rotates freely with the flow. Thus, the 3-dimensional shape of the particle can be determined during the dissolving process by taking sequential images.

It has been shown that the dissolution rate curves obtained by means of the invention and established reference chemical analyses are practically identical, demonstrating the applicability of the invention in practice. That combined with smaller source material consumption, accurate data, shorter measurement times, and the fact that no validation of new chemical methods are needed, means that the present method provides a significant improvement for early-stage development of pharmaceutical substances, compared to existing methods. Needless to mention, all this makes the introduction of new drug products on the market faster and more cost-effective.

The dependent claims are directed to selected embodiments of the invention.

According to one embodiment, the trapping of the particle in the particle trapping zone is entirely achieved by hydrodynamic motion of the dissolution medium in the vessel. This means that no additional trapping means that exert a force on the particle, are needed or used.

According to one embodiment, the trapping of the particle in the particle trapping zone is partly based on hydrodynamic motion of the dissolution medium in the vessel and assisted by using other means, such as optical, acoustic or electromagnetic trapping means, exerting a force on the particle.

In other words, the trapping of the particle in the particle trapping zone can be achieved by geometry of the vessel combined with liquid flow in/through the vessel, by optical particle trapping means, by acoustic particle trapping means, by electromagnetic particle trapping means, or any combination thereof.

According to one embodiment, the dissolution medium is rotated in the vessel for forming the particle trapping zone in the rotating flow. The rotation can be achieved for example in a dissolution chamber with at least one input of dissolution medium to the dissolution chamber and at least one output of dissolution medium from the dissolution chamber, the input(s) and output(s) being positioned so that a rotating flow with said particle trapping zone is formed into the dissolution chamber as the dissolution medium is pumped through the input(s) to the output(s).

According to one embodiment, the particle trapping zone is formed at the axis of rotation of the dissolution medium.

According to one embodiment, the dissolution chamber can be cylindrical or conical in shape.

According to one embodiment, the dissolution chamber comprises at least two inputs of dissolution medium in horizontal orientation at a lower half thereof and a vertical output of dissolution medium at higher half thereof. This produces an upwardly whirling motion of liquid, with a stabile particle trap close to the bottom of the chamber.

According to one embodiment, the dissolution medium is fed continuously through the vessel using a pump. The energy provided by the pump can be used to form the hydrodynamic motion producing the particle trap.

According to one embodiment, the dissolution medium is fed into the dissolution vessel during a limited time or in a pulsating way. The hydrodynamic flow is in this way used to trap the particle and to bring the particle into the imaging area, while the imaging is performed under stagnant conditions.

According to one embodiment, the dissolution medium is rotated in the vessel at least partly by using a rotatable member provided in contact with the dissolution medium, or through rotating the dissolution vessel. The rotatable member can be e.g. a blade or plate.

The method can be run simultaneously (in parallel) or in series (successively) in a plurality of similar vessels in which particles are trapped and their dissolution properties determined.

The particle whose dissolution properties are examined can comprise any chemical, biological or biochemical particle. In particular, it can be a pharmaceutical substance having an initial size of 5-500 μm or more, even up to 1 mm, when using microscopic imaging. Consequently, it is possible to examine smaller particles, having for example an initial size of 100 nm, when using e.g. in situ nanoscopy. Thus, the size of the particle to be examined depends on the chosen imaging method.

The present system preferably comprises the vessel with the dissolution chamber and may comprise at least one transparent wall portion, means for producing a hydrodynamic flow with the particle trapping zone inside the chamber and a imaging device integrated into one or many vessel walls, or positionable at the transparent wall portion for providing a time series of images of the particle while being trapped. In addition, the system may comprise computerized and automated image analysis means, including software and algorithms, adapted to determine at least one dissolution property of the particle based on the series of images.

Definitions

The term "particle" covers also the particle residue formed when the original particle fed to the system dissolves. The invention also covers the examination of several particles simultaneously, even if a singular form of the particle is used.

The term "particle trapping zone" means a zone inside the dissolution vessel in which particles to be studied remain during the test such that they can be imaged several times at intervals. In particular, the particle trapping zone is a volume, which the particle is unable to leave if the motion of fluid surrounding the particle is kept essentially constant. In an ideal case, the particle "floats" or rotates in place, although in practice some movement in any direction may take place. The zone typically has a volume which is a fraction of the whole volume of the chamber. The fraction may be for example 1:10 or less, in particular 1:50 or less, depending on the size of the particle and the chamber. The zone is preferably apart from vessel walls but may also be touching one or more wall. Of practical importance is that the zone has boundaries smaller than the field-of-view of the imaging unit used. This ensures that every time an image is taken, the size and shape of the particle and/or mass released from the particle can be determined.

Dissolution rate, intrinsic dissolution rate and solubility are established concepts in the field of chemistry. Intrinsic dissolution rate (IDR) refers to dissolution rate normalized to the surface area of the particle. Instead of these three preferred ones, the "dissolution property" can be also some other quantity which is related to the physical or chemical behavior or composition of the particle or the dissolution medium during the dissolution process.

Next, embodiments of the invention and advantages thereof are discussed in more detail with reference to the attached drawings.

DETAILED DESCRIPTION OF EMBODIMENTS

System and Method Overview

Figure 1A:
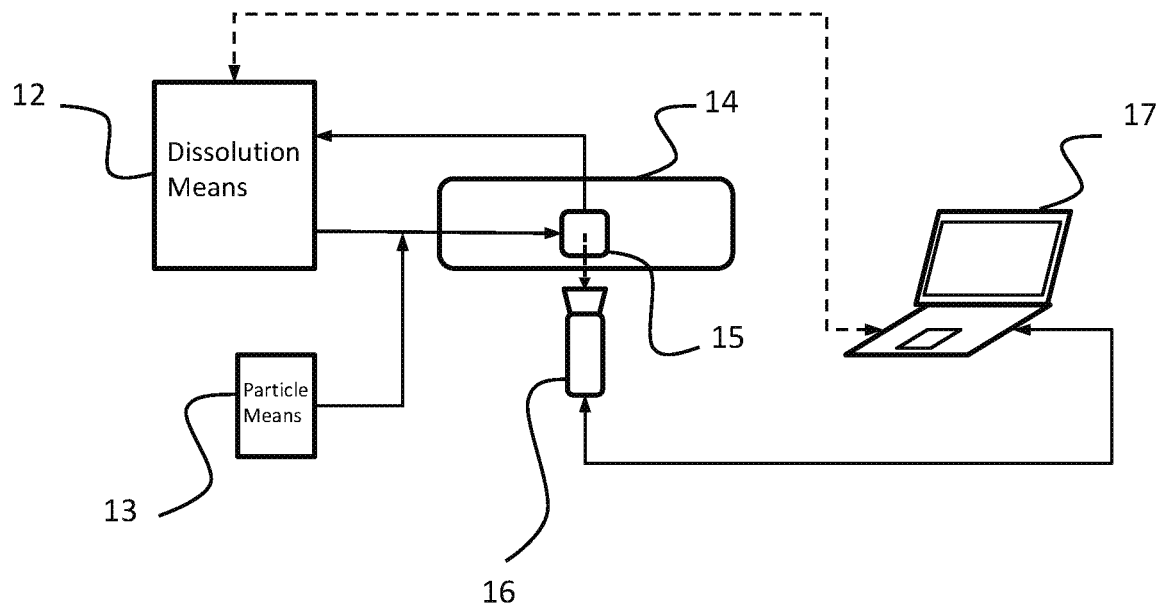
FIG. 1A shows a schematic block diagram of the present system according to one embodiment.

FIG. 1A shows an overview of basic components of the present testing system according to one embodiment. The system comprises a dissolution vessel 14 comprising a dissolution chamber 15. The chamber 15 is connected to a source 12 of dissolution medium, the source 12 preferably comprising a pump or the like device capable of feeding dissolution medium in a controlled manner (e.g. continuous, pulsating or momentary feed) to the chamber 15. The source 12 may also comprise a mixer unit for continuously mixing multiple solvents in desired ratios. There may be provided a fresh feed of dissolution medium or a closed circulation. There is also provided a means 13 for feeding one or more particles whose dissolution properties are to be tested to the dissolution chamber 15 to be trapped therein and imaged as it/they dissolve(s) and/or interact (e.g. cells).

There is also provided a imaging device 16, which is capable of taking a sequence of images of the particle(s) trapped in the chamber 15. The imaging device 16 is aligned with a transparent wall of the chamber or built-in into the vessel.

The testing process is controlled and images analyzed using a computer 17, which is functionally connected with and capable of controlling the source of dissolution medium, mixer, pump and the camera device 16. The computer 17 also comprises software means capable of receiving, storing and analyzing the images taken by the imaging device 16. In particular, the computer comprises software means capable of determining the size and/or shape and, thus, the dissolution rate, intrinsic dissolution rate and/or solubility of the particle in the dissolution medium.

In addition to the components described above, the system preferably comprises means for measuring and regulating the temperature and pH of the dissolution medium and/or means for removing gas from the dissolution medium before feeding to the chamber. The former is necessary for ensuring measurement results commensurate with other measurements and the latter for preventing accumulation of gas in the channels or chambers of the system or interfering the dissolution process.

Figure 1B:
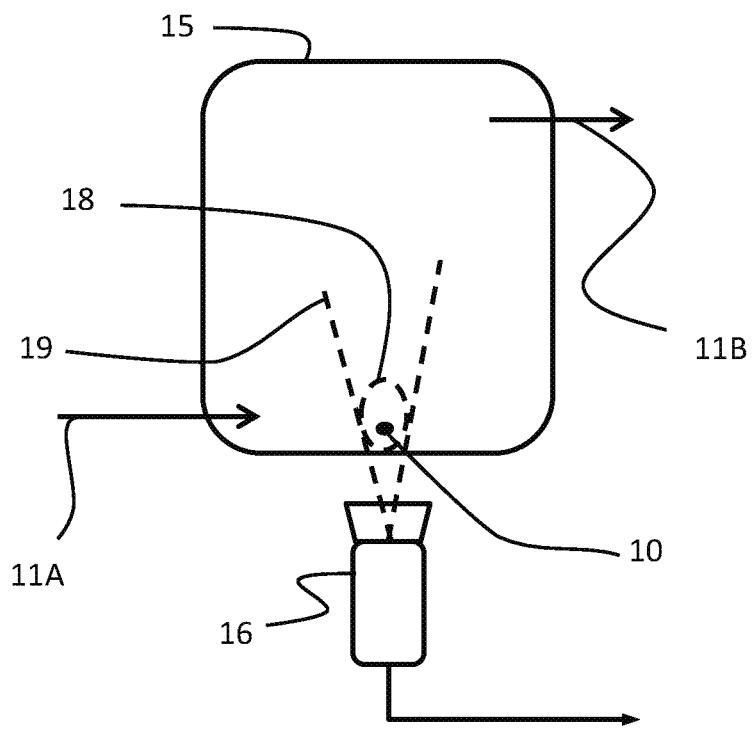
FIG. 1B shows a schematic view of a dissolution chamber in imaging condition with a particle trapped in a particle trapping zone.

FIG. 1B shows a schematic representation of a particle trapping zone 18 in the dissolution chamber 15 and the principle of the imaging arrangement. The feed of dissolution medium is shown as arrow 11A and exit of dissolution medium as an arrow 11B. There is provided a trapped particle 10 in the particle trapping zone 18 formed in the chamber 14. The imaging device 16 has a field-of-view 19, which covers the whole particle trapping zone 18, so that an image of the particle 10 is obtained for further analysis every time the imaging device 16 is triggered.

According to one embodiment, a single particle at a time is trapped to the chamber.

According to one embodiment, the trapped particle rotates in place, allowing for imaging thereof from many perspectives from one imaging direction, allowing a 3D-reconstruction of the particle topology and morphology.

According to one embodiment, the trapped particle is imaged from multiple directions simultaneously, using several imaging capturing devices or reflecting surfaces.

Figure 1C:
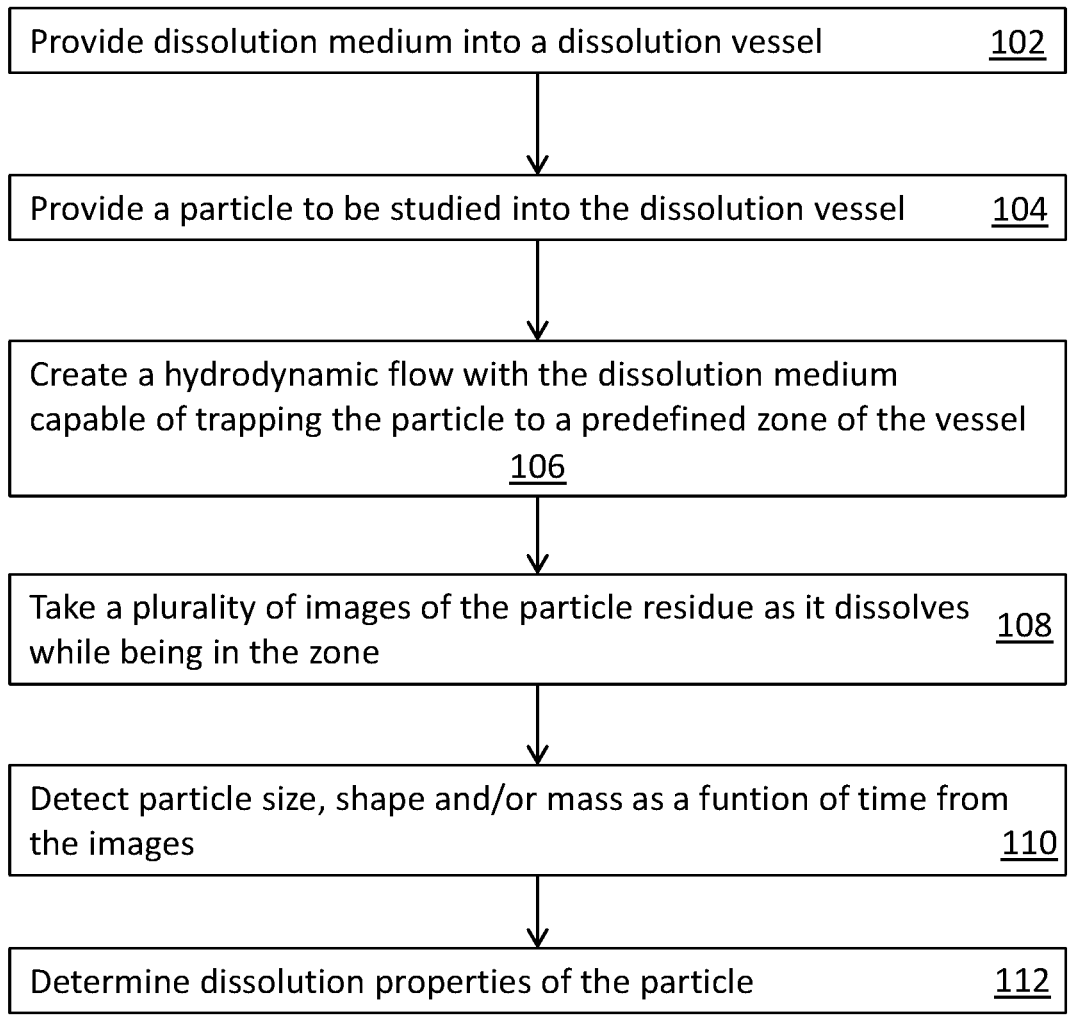
FIG. 1C illustrates a flow chart of the present method according to one embodiment.

FIG. 1C shows as a flow chart an overview of the present method. First, the dissolution vessel is filled with dissolution medium, such as water or buffer solution (step 102). Then the particle is brought to the vessel and immersed into the dissolution medium (step 104). Next, the dissolution medium is caused to move in a way that produces the particle trapping zone inside the vessel (step 106). The particle dissolves and a solid residue thereof remains in the particle trapping zone (at least until some minimum size is reached at which the particle residue is light enough to go with the flow outside the trapping zone). The residue is imaged sequentially in order to detect its size, shape and/or mass loss (step 108). The time-point of imaging or the time interval between the images are/is also recorded. The change in shape and the size/mass loss as a function of time is determined preferably using computerized image analysis means (step 110). Finally, the dissolution property of interest is determined (step 112) using the information on the size, shape and/or mass loss as a function of time.

According to one embodiment, representing an example of a flow-through configuration, the testing method comprises one, some or all of the following steps or features:
providing a dissolution vessel having a dissolution chamber with an input channel for liquid dissolution medium and an output channel for liquid dissolution medium,
pumping liquid dissolution medium through the dissolution chamber with constant flow rate, or when desired, via said input channel and output channel such that a hydrodynamic flow, preferably at least partly rotational flow, capable of trapping a solid particle in a sub-volume of the chamber (particle trapping zone), is formed.
providing a particle dissolvable in the dissolution medium into the chamber, preferably via the input channel in order to trap the particle into the sub-volume (the particle can be provided into the chamber before or after starting the solvent flow),
imaging the particle/s through a transparent portion of the vessel, or with a built in imaging device, aligned with the sub-volume for providing a plurality of sequential images of the particle/s while the particle/s move(s) with the flow, stay(s) stagnant or move freely, but remain within the sub-volume, and
determining dissolution rate, intrinsic dissolution rate or solubility of the particle based on the images of the particle as a function of time, in particular change of particle size and shape as it dissolves.

According to another embodiment, representing an example of a closed chamber configuration, the testing method comprises one, some or all of the following steps or features:
providing a dissolution vessel comprising a dissolution chamber capable of holding liquid dissolution medium and means, such as a rotatable blade or plate, for rotating the dissolution medium,
filling the dissolution chamber with liquid dissolution medium,
providing a solid particle to be studied into the chamber in contact with the dissolution medium,
rotating the dissolution medium with said means for rotating such that a hydrodynamic flow trapping the solid particle in a sub-volume of the chamber (particle trapping zone), is formed.
imaging the particle/s through a transparent portion of the vessel, or with a built in imaging device, aligned with the sub-volume for providing a plurality of sequential images of the particle/s while the particle/s move(s) with the flow, stay(s) stagnant or move freely, but remain within the sub-volume, and
determining dissolution rate, intrinsic dissolution rate and/or solubility of the particle based on the images of the particle as a function of time, in particular change of particle size and shape as it dissolves.

According to one embodiment, representing an example of a flow-through or closed chamber configuration, the testing method comprises one, some or all of the following steps or features:
providing a vessel having a chamber with an input channel for liquid medium and an output channel for liquid medium,
pumping liquid medium through the chamber with constant flow rate, or when desired, via said input channel and output channel, or rotating the member, such that a hydrodynamic flow, preferably at least partly rotational flow, capable of trapping one or many particles in a sub-volume of the chamber (particle trapping zone), is formed.
providing a particle into the chamber, preferably via the input channel in order to trap the particle into the sub-volume (the particle can be provided into the chamber before or after starting the solvent flow),
imaging the particle/s through a transparent portion of the vessel, or with a built in imaging device, aligned with the sub-volume for providing a plurality of sequential images of the particle/s while the particle/s move(s) with the flow, stay(s) stagnant or move freely, but remain within the sub-volume, and
determining properties and reactions and interactions of the particle/s based on the images of the particle/s as a function of time, such as cell-cell or cell-drug reactions/interactions.

Exemplary particles and dissolution medium suitable for the present method and system and exemplary implementations of the dissolution vessel, imaging arrangement and image analysis methods are described below.

Particles and Dissolution Medium

The particles to be studied can be solid, such as e.g. powder particles, crystals, pellets or granules or they may be biological or biochemical particles, such as cells or polymers. According to one embodiment of the present invention the particle is non-dissolvable, such as a biological cell. In such case the dissolution medium functions as a liquid medium and the studied dissolution properties can be other physical or chemical properties of the particle/s and/or their reaction/s and interaction/s. The particles to be studied are solid and may have an original size of 200 nm-1 mm, usually at least 5 µm, in particular 10-1000 µm. Most typically, particles of 10-500 µm are used. However, size of the particle may be smaller or bigger depending on the imaging method, as described earlier. "Size" refers to maximum dimension of the particle, such as diameter in the case of spherical particles. Too small (light) particles tend to go with the flow outside the particle trapping zone, when using microscopic imaging. In addition, with optical imaging methods the accuracy of particle size determination decreases with particle size due to practical or theoretical imaging resolution constraints. Large particles, however, increase starting material consumption and may require higher flow rates of the solvent in order to take the correct position in the dissolution chamber. Also the imaging field-of-view may set upper limit for particle size.

The original mass of the particle can be for example 0.001-1 mg.

The particles can be essentially spherical, but also other shapes, such as irregular shapes and rod shapes, for example, are usable. Rotation of the particles in the chamber allows for imaging them from all directions, even from one detection angle, and therefore size and shape (volume and surface area) determination of even complex shapes is possible.

The particles can comprise or be comprised of ionic, polar, neutral or polymeric compounds as the dissolvable matter, or the particles can be non-dissolvable.

In particular, the particles can be chemical, biological or biochemical, of which pharmaceutical substances or candidates for pharmaceutical substances are probably most important, as decent dissolution rate and solubility is typically required from them.

The dissolution medium is typically water and/or ethanol or water-based, such as a buffer solution and biorelevant media, at least in pharmaceutical studies, but in principle any other solvent can be used in the present invention.

Dissolution Vessel

Figure 2A:
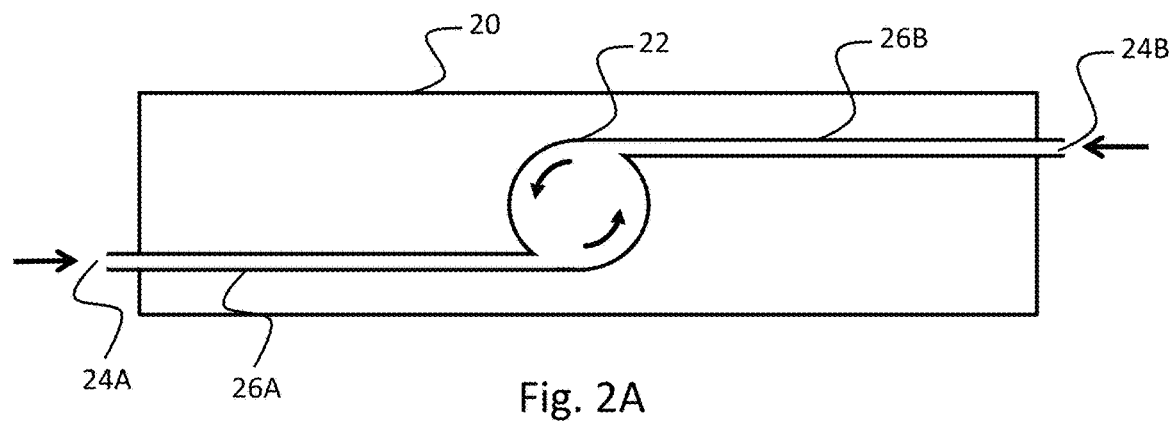
FIGS. 2A and 2B show top and side views, respectively, of a flow-through dissolution vessel according to one embodiment of the invention.
Figure 2B:
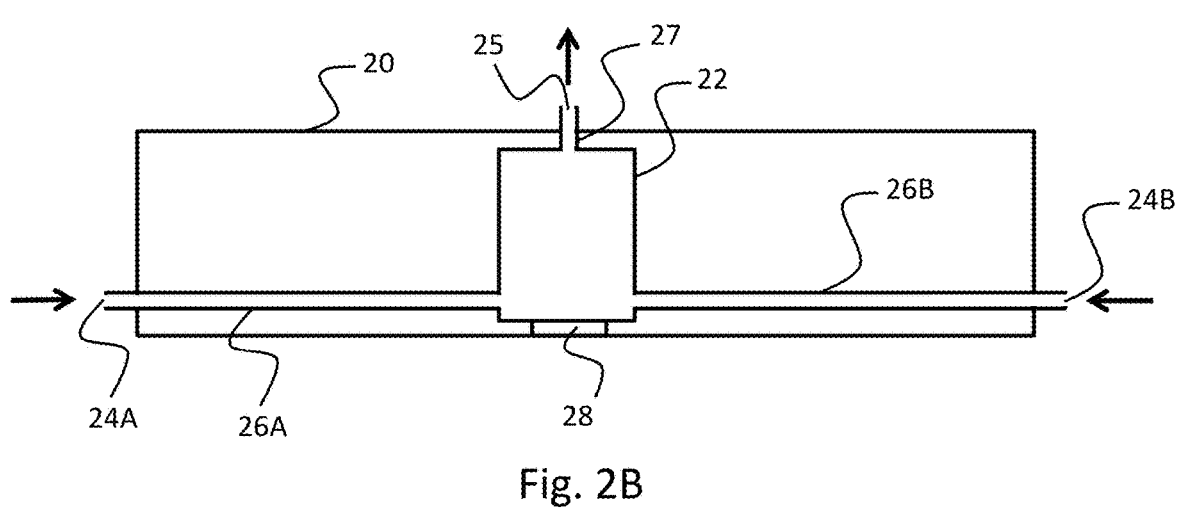

FIGS. 2A and 2B illustrate one embodiment of the dissolution vessel. The vessel 20 comprises a body defining a cylindrical dissolution chamber 22 and two input channels 26A, 26B to the chamber 22 for the dissolution medium. The input channels 26A, 26B are arranged tangentially to the (vertical) side walls of the chamber 22 and on different (opposite) sides thereof so that the dissolution medium fed to the chamber 22 starts to rotate. The input channels 26A, 26B are connected at their respective feeding ends 24A, 24B to a pump or other device (not shown) capable of generating the flow. As shown in FIG. 2B, the input channels 26A, 26B are preferably connected close to the bottom of the chamber 22, or at least to the lower half thereof. This assists in creating a hydrodynamic flow inside the chamber 22 that comprises the particle trapping zone.

On one side, here top side, of the chamber 22, there is a dissolution medium output channel 27 for exiting equal amount of medium from the chamber that is pumped in though the input channels 26A, 26B. The output channel 27 is connected at its output end 25 to the pump (closed circulation) or to a drain or used medium reservoir.

There is provided an imaging window 28, i.e. a transparent wall portion, at the bottom wall of the dissolution chamber. Naturally, the whole vessel may be made from transparent material, whereby a separate window is not needed, or the imaging system may be integrated into the vessel walls. However, a separate window may assist in controlling the ambient light conditions during imaging. There may also be provided a separate window for illumination of the sample (e.g. backlight illumination).

The vessel of FIGS. 2A and 2B is capable of producing, while feeding, constantly or when desired, dissolution medium through the input channels 26A, 26B and simultaneously removing dissolution medium through the output channel 27, a whirl in the chamber 22 that keeps the particle trapped in place.

The dimensions of the chamber according to FIGS. 2A and 2B can be for example the following: radius 5 mm and height 10 mm. Input channels can be arranged at height 0 mm tangentially as shown in the figures. The flow rate of aqueous dissolution medium in such chamber can be e.g. 5-25 ml/min.

Figure 3A:
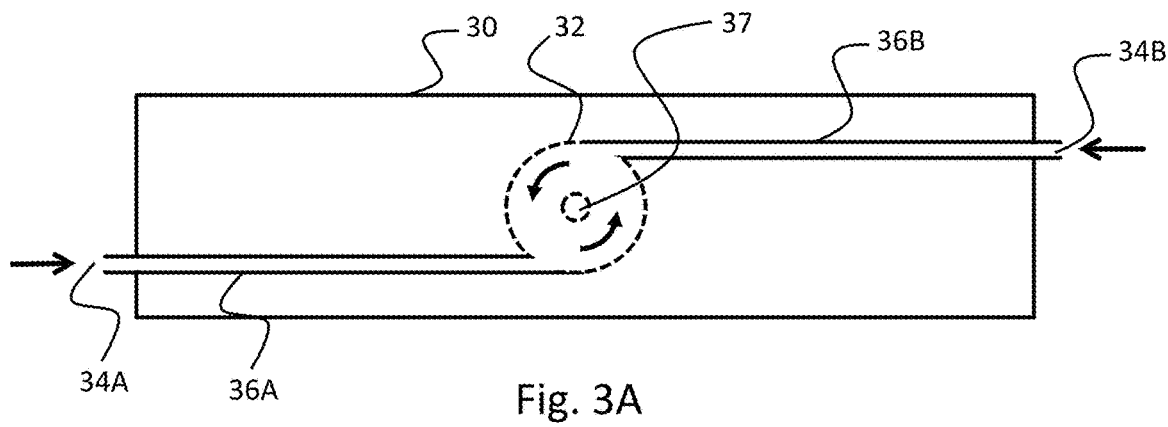
FIGS. 3A and 3B show top and side views, respectively, of a flow-through dissolution vessel according to another embodiment of the invention.
Figure 3B:
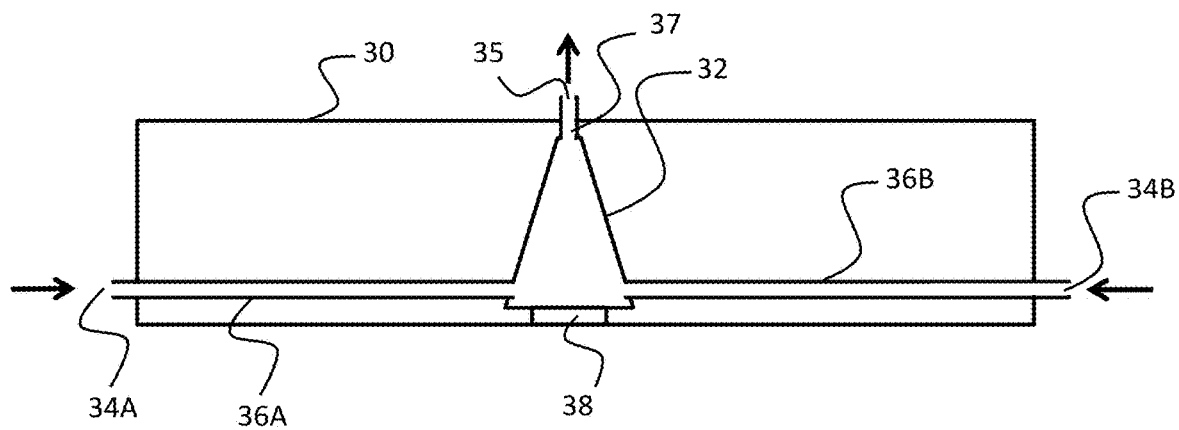

FIGS. 3A and 3B illustrate an alternative flow-through vessel 30, which is otherwise similar to that of FIGS. 2A and 2B but comprising a conical dissolution chamber 32 instead of cylindrical one. The chamber 32 is has its broad end at the bottom and it tapers towards the top. The shape can be a full cone or a truncated cone, the latter variation being shown in the figures. The input channels 36A, 36B are connected to the chamber 32 in the vicinity to the broad end of the chamber 32, whereas the output channel 37 is connected to the narrow end. The inputs 34A, 34B, output 35, and imaging window 38 are as in the embodiment of FIGS. 2A and 2B. A conical chamber has the benefit over a cylindrical one that the whirl of the dissolution medium produced in the chamber 32 is intensified towards the top of the chamber, keeping the particle trapping zone lower and more stable close to the bottom of the chamber 32. The cone can also be used in an inverted configuration with the narrow end downwards.

The dimensions of the chamber according to FIGS. 3A and 3B can be for example the following: radius at bottom 5 mm, radius at top 0.5 mm and height 10 mm. Input channels can be arranged at height 0 mm tangentially as shown in the figures. The flow rate of aqueous dissolution medium in such chamber can be e.g. 5-15 ml/min.

Instead or in addition to a pumping device external of the dissolution vessel and continuous through flow, the flow of dissolution medium in the dissolution chamber can also be achieved using other means, such as a rotatable blade or plate in contact with the dissolution medium. According to one embodiment, illustrated in FIGS. 4A and 4B, the dissolution vessel 40 comprises a cylindrical dissolution chamber 42 and a circular plate 43 placed on top of the dissolution chamber 42 such that it comes into contact with the liquid inside the chamber 42. The plate 43 is rotated using a shaft 41 on the surface of the liquid such that friction between the plate 43 and liquid make the liquid rotate too. A vortex or the like hydrodynamic flow is then formed in the rotating liquid, like in the embodiments of FIGS. 2A, 2B, 3A and 3B, producing a stable particle trapping zone therein. The imaging window 48 is in this example positioned at the bottom wall of the dissolution chamber 42, but may locate on a side wall as well, or the imaging device may be integrated into the vessel walls.

Figure 4A:
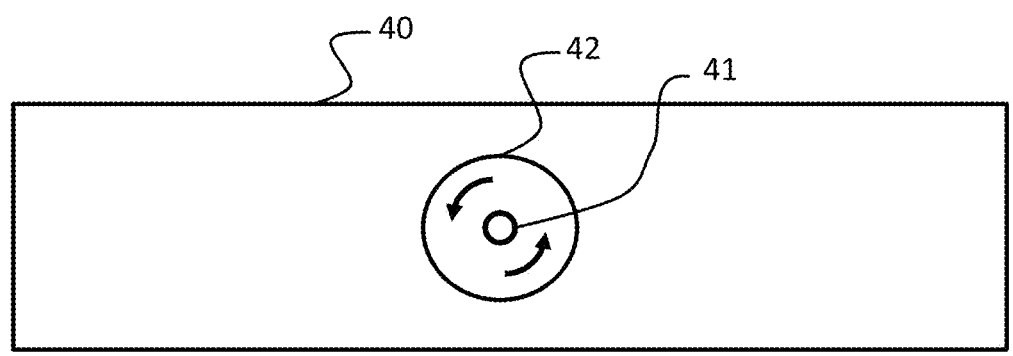
FIGS. 4A and 4B show top and side views, respectively, of a closed dissolution vessel according to one embodiment of the invention.
Figure 4B:
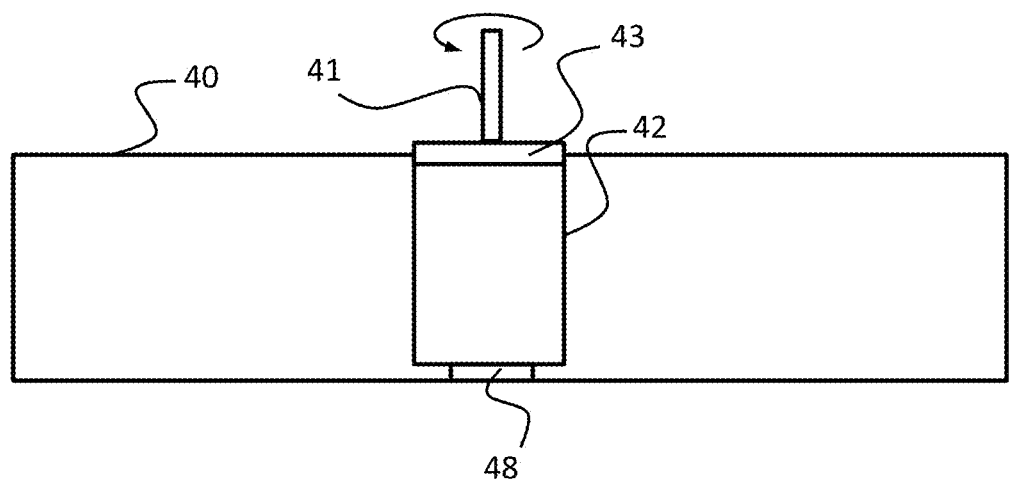

The dissolution chamber of FIGS. 4A and 4B is closed in the sense that no through-flow of dissolution medium is needed during the dissolution test. Naturally, there may be one or more inputs or outputs (not shown) to aid filling of the chamber. The plate 43 can also be temporarily removable to allow for filling of the chamber from the top side thereof.

According to one embodiment, the dissolution vessel comprises a plurality of dissolution chambers, i.e. is a multi-chamber entity. Such entity allows for conducting several dissolution tests in parallel or in series. The vessel can be for example dimensioned and/or pitched according to standard (SBS) microplates to allow for maximum compatibility with automatic plate manipulators and/or material dispensers and/or imaging systems.

According to one embodiment, the dissolution vessel comprises a plate with several open or closed wells or cavities each forming a dissolution chamber capable of trapping a single particle. Each of the chambers comprise transparent portion through which the imaging can be carried out, or contain a built in imaging device. The chambers may be positioned in a one- or two-dimensional array. The chambers can be for example shaped as described above in connection with FIGS. 2-4. In the case of through-flowing dissolution medium, such as in FIGS. 2-3, there should be arranged separate fluid inputs and outputs for each chamber. The inputs and outputs may be connected in parallel or in series, most preferably in parallel to avoid mixing of contents of the chambers.

All of the vessel designs described above are capable of producing a particle trapping zone based on hydrodynamic behavior of the dissolution medium only. Instead of or in addition to hydrodynamic fluid trapping effect, the trapping of the particle can be cause or assisted by one or more other effects. As concerns existing techniques for manipulating single particles in fluidic environment, and which can be used in the context of the present invention, WO 2008/068680 is referred to. The document provides a system which is capable of for example orienting a single particle in a fluid. The particle is placed in a laminar flow, where it can be trapped and moved to different positions using for example optical tweezers, dielectrophoresis, acoustic mechanisms, deformation of the fluid channel or electric or magnetic fields. The same mechanisms, in particular optical, acoustic and electromagnetic or electrostatic, are usable in embodiments of the present invention to stabilize the particle position during the test. In particular, these mechanisms can be used together with the hydrodynamic flow to ensure staying of the particle in the chamber and stability of the particle during the start and/or maintenance of the flow dissolution medium.

Imaging

The imaging can be carried out by any suitable technique capable of obtaining information on the deformation of the particle as it dissolves. Examples include optical microscopy (producing a projection image of the physical size of the particle), fluorescence microscopy (producing an image corresponding to or signal proportional to fluorescent emission of the particle/substance upon suitable excitation), ultraviolet imaging (producing an image corresponding to or signal proportional to ultraviolet light emitted by the particle/substance), Raman-spectroscopy (producing an image based on Raman scattering of the particle), interferometry (producing an image based on the interference pattern, produced by waves interacting with the sample), diffraction and dynamic light scattering (giving data about the particle size, determined by the scattering of light).

The imaging techniques are as such known per se and can be directed to small volumes as required by the present invention to get information on the dissolution of individual particles. Also suitable imaging devices are commercially available or relatively straightforwardly customizable for the present needs. What needs to be taken care of is that the vessel wall or window therein is transparent to the radiation used by the imaging system. That is, the vessel itself must not significantly attenuate or alter the radiation to be recorded by the imaging device, for example optical wavelengths in the case of an optical microscopy, or the detector must be calibrated accordingly.

The imaging may be based on direct illumination, backlight illumination, or self-illumination of the sample.

Image Analysis

The images obtained from the imaging device are stored on an analysis unit, such as a computer, where they are analyzed, using appropriate software and algorithms, in order to determine the dissolution property desired. The analysis depends on the imaging technique used, since the origin of the recorded radiation is different.

In the case of optical microscopy, each of the images obtained comprise a "micrograph", i.e. projection image, of the particle at different stages of the dissolution process and potentially at different orientations. In one embodiment, the processing comprises:

determining sizes of the projection of the particle residue, i.e., based on the cross-sectional surface areas thereof, from the successive images, determining shapes of the projection of the particle residue, i.e., based on the cross-sectional surface areas thereof, from the successive images, estimating the relative or absolute mass of the particle residue (or mass released from the particle compared with the first image, or estimated initial particle size) based on data from the cross-sectional surface areas, determining the dissolution rate based on the masses of the particle residues and information on imaging times, determining the intrinsic dissolution rate based on the masses of the particle residues, imaging times and surface area information extracted from the images, determining the solubility of a substance based on the masses of the particle residues and imaging times extracted from the images.

According to one embodiment, computation of the desired dissolution property or properties is carried out in real time as the dissolution and imaging proceeds, based on the data obtained until that. The result may be a rough approximate in the beginning and get more accurate as there is more data available. The data analysis may also be iterative and a 3D particle reconstruction with topographical and morphological information can be made from the image data.

According to another embodiment, the computation of the dissolution property or properties is carried out only after the dissolution process has reached a predefined point, after which the process can typically be terminated.

Figures 5A, 5B:
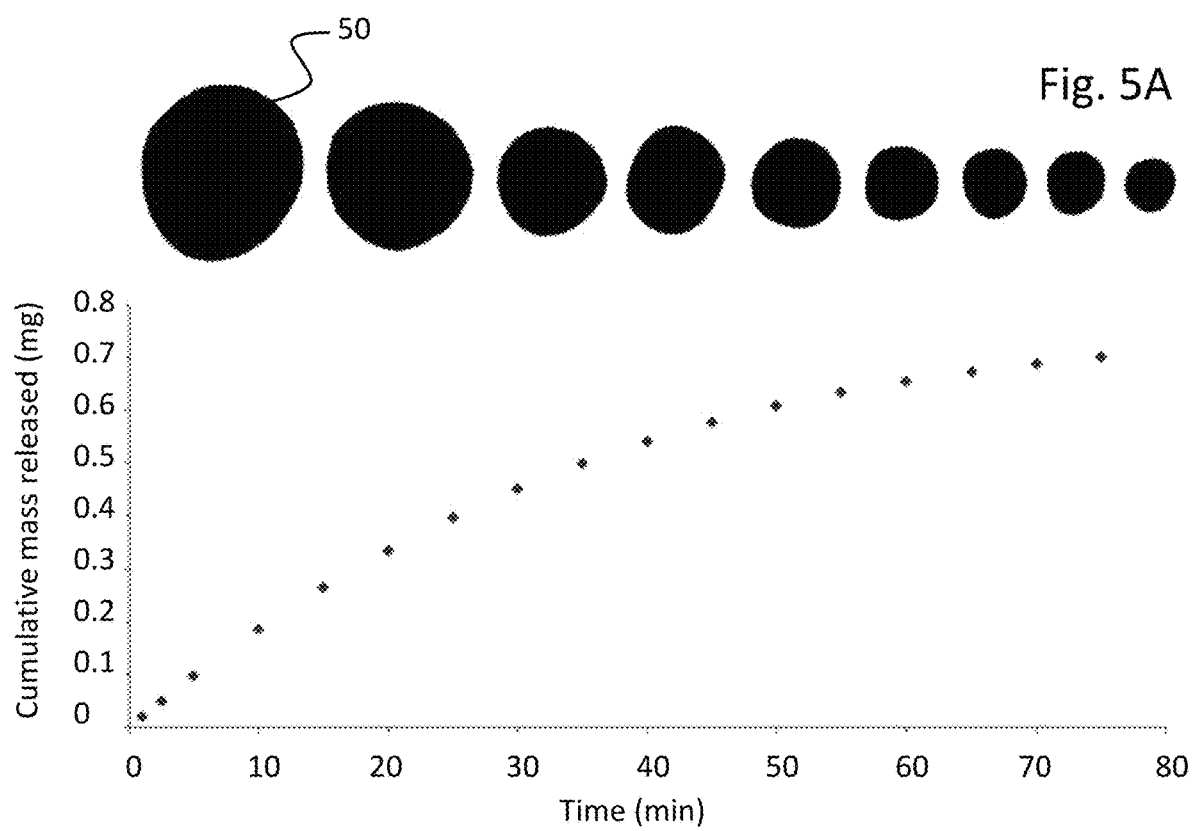
FIGS. 5A and 5B show a series of particle size and graph of cumulative mass released vs. time, respectively, obtained in an exemplary dissolution test using the principle of the invention.

FIG. 5A shows an exemplary image series of a particle 50 optically imaged using the present invention during dissolution while being trapped in a hydrodynamic flow trap. Leftmost is a projection image of the particle 50 in the beginning of the method and rightmost after about 80 minutes of dissolving (see time scale in FIG. 5B). As can be seen, as the cross-sectional area of the particle 50 decreases with time, relative or absolute mass released from the original particle 50 can be estimated. One can for example use the information that the volume of the particle 50 is proportional to $r^3$ (r=radius of the particle) and the cross-sectional area proportional to $r^2$.

FIG. 5B shows a graph of the estimated cumulative mass released as a function of time (using a shorter imaging interval than shown in FIG. 5A). As can be seen, the mass released increases monotonically and saturates towards the original mass of the particle 50.

The invention claimed is:

1. A method for determining dissolution properties of a particle, comprising providing into a vessel, dissolution medium capable of dissolving the particle, providing the particle into said vessel in contact with the dissolution medium for dissolving the particle, imaging the particle during dissolution for providing a plurality of sequential images of the particle, and determining at least one dissolution property of the particle based on said sequential images, wherein the particle is trapped in a particle trapping zone formed at a predetermined location in the vessel, and the imaging is carried out by an in-built imaging system or through a transparent portion of the vessel when the particle dissolves while being trapped in said particle trapping zone, and wherein the trapping of the particle in the particle trapping zone is partly or entirely achieved by hydrodynamic motion of the dissolution medium in the vessel, and wherein the hydrodynamic motion comprises rotation of the dissolution medium in the vessel.

2. The method according to claim 1, wherein trapping of the particle in the particle trapping zone is entirely achieved by hydrodynamic motion of the dissolution medium in the vessel.

3. The method according to claim 1, wherein trapping of the particle in the particle trapping zone is partly based on hydrodynamic motion of the dissolution medium in the vessel and assisted by using optical, acoustic or electromagnetic trapping means exerting a force on the particle.

4. The method according to claim 1, wherein the vessel comprises a dissolution chamber having at least one input of dissolution medium to the dissolution chamber and at least one output of dissolution medium from the dissolution chamber, the input(s) and output(s) being positioned so that a rotating flow with said particle trapping zone is formed in the dissolution chamber.

5. The method according to claim 4, wherein the dissolution chamber is cylindrical or conical in shape, and comprises at least two inputs of dissolution medium in a horizontal orientation at a lower half thereof and a vertical or horizontal output of dissolution medium at an upper half thereof.

6. The method according to claim 1, wherein the dissolution medium is rotated in the vessel at least partly using a rotatable member provided in contact with the dissolution medium, or through rotating the vessel.

7. The method according to claim 1, further comprising feeding the dissolution medium in a controlled manner through the vessel.

8. The method according to claim 1, wherein the particle has an initial size of 100 nm-1 mm.

9. The method according to claim 1, wherein the vessel is located in a plate comprising a plurality of further vessels in which particles are trapped and dissolution properties determined either sequentially or in parallel.

10. The method according to claim 1, wherein the particle comprises a chemical, biological or biochemical particle.

11. The method according to claim 10, wherein the particle comprises a pharmaceutical substance or a lead or candidate for a pharmaceutical substance.

12. The method according to claim 1, further comprising determining the dissolution rate, intrinsic dissolution rate and/or solubility of the particle as said dissolution property.

13. The method according to claim 1, wherein the particle is a biological cell.

14. The method according to claim 1, wherein the particle trapping zone has a volume having a ratio of 1:10 relative to a whole volume of the vessel.

15. A system for determining dissolution properties of one or more particles, comprising a dissolution vessel comprising a dissolution chamber capable of holding dissolution medium, wherein the system is provided with means for producing in the dissolution chamber a particle trapping zone, where the one or more particles remain essentially in a steady position, the dissolution vessel comprises an in-built imaging system and/or at least one transparent portion configured for imaging the one or more particles trapped in the particle trapping zone from outside of the vessel, and a computing device configured for determining at least one dissolution property of the one or more particles based upon image data from said imaging, wherein the means for producing the particle trapping zone are partly or entirely based on producing a hydrodynamic flow in the dissolution chamber that causes the particle to remain in said steady position, wherein said dissolution vessel further comprises one or more input channels for feeding dissolution medium to the dissolution chamber and one or more dissolution medium output channels for removing dissolution medium from the dissolution chamber such that upon rotation of the dissolution medium, a rotating flow with the particle trapping zone at an axis of rotation of the dissolution medium is formed inside the dissolution chamber.

16. The system according to claim 15, wherein the one or more input channels are connected to a lower half of the dissolution chamber and the one or more output channels are connected to an upper half of the dissolution chamber.

17. The system according to claim 15, wherein the dissolution chamber is conical in shape.

18. The system according to claim 15, wherein the at least one transparent portion is located at a top wall, a bottom wall, or aside wall of the dissolution chamber.

19. The system according to claim 15, further comprising an imaging device, built into walls of the vessel or configured to image through the at least one transparent portion and having a field of view directed at the particle trapping zone for providing a plurality of sequential images of the particle during dissolution, reactions or interactions.

20. The system according to claim 19, further comprising computerized image analysis means functionally connected to the imaging device and adapted to determine at least one dissolution property, or other physical or chemical property, of the particle based on said sequential images.

21. The system according to claim 15, further comprising at least one of the following features:

a pump capable of flowing the dissolution medium continuously through the dissolution chamber, a mixing unit capable of continuously mixing multiple liquids in desired ratios, means for regulating the temperature of the dissolution medium, means for regulating the pH of the dissolution medium, and means for removing gas from the dissolution medium.

22. A method for determining dissolution properties of a particle comprising:

maintaining a stabilized position of the particle via rotational flow of a dissolution medium about the particle;

imaging the particle in the stabilized position to generate a plurality of sequential images of the particle, and determining at least one dissolution property of the particle based on the plurality of sequential images.

* * * * *